United States Patent
Brenner et al.

(10) Patent No.: US 6,670,145 B2
(45) Date of Patent: Dec. 30, 2003

(54) **METHOD FOR DETECTION OF TOTAL COLIFORMS AND *E. COLI***

(75) Inventors: Kristen P. Brenner, Cincinnati, OH (US); Clifford C. Rankin, Dayton, OH (US); Yvette R. Roybal-McKenna, Gilbert, AZ (US); Alfred P. Dufour, Cincinnati, OH (US)

(73) Assignee: The United States of America as represented by the Administrator of the Environmental Protection Agency, Washington, DC (US)

(*) Notice: Subject to any disclaimer, the term of this patent is extended or adjusted under 35 U.S.C. 154(b) by 70 days.

(21) Appl. No.: 09/924,950

(22) Filed: Aug. 9, 2001

(65) Prior Publication Data

US 2002/0048780 A1 Apr. 25, 2002

Related U.S. Application Data

(63) Continuation of application No. 09/369,173, filed on Aug. 5, 1999, now Pat. No. 6,306,621, which is a continuation-in-part of application No. 08/117,342, filed on Sep. 7, 1993, now Pat. No. 6,063,590, which is a continuation of application No. 07/793,881, filed on Nov. 18, 1991, now abandoned.

(51) Int. Cl.[7] .............................. C12Q 1/04; C12Q 1/10; C12N 1/20
(52) U.S. Cl. .............................. 435/29; 435/4; 435/33; 435/34; 435/38; 435/253.6
(58) Field of Search ................................ 435/4, 29, 33, 435/34, 38, 253.6

(56) References Cited

U.S. PATENT DOCUMENTS 6,306,621 B1 * 10/2001 Brenner et al. ............... 435/38

OTHER PUBLICATIONS

Duncanson, "Membrane Filter Method for the Enumeration of Chlorine Damaged Coliforms in Drinking Water" *Technology Conference Proceedings: Water Quality Technology Conference,* Nov. 16–20, 1996.

Stevens & Joynson, "Direct inoculation into media containing bile salts and antibiotics is suitable for the detection of acid/salt stressed *Escherichia coli* 1057:H7", *Applied Biology,* 27, pp 147–151 (1998).

Petzel & Hartman, Monensin–Based Medium for Determination of Total Gram–Negative Bacteria & *Escherichia coli, Applied & environmental Microbiology,* pp 925–933 (Apr. 1985).

Freier & Hartman, "Improved Membrane Filtration Media for Enumeration of Total Coliforms & *Escherichia coli* from Sewage & Surface Waters", *Applied & Environmental Microbiology,* pp 1246–1250 (Jun. 1987).

*Fundamentals of Microbiology,* (Ninth Edition) W.B. Sanders Co, Philadelphia (1974) pp 468, 478 and 479.

Fainstein, et al., "Invitro Susceptibilities of *Aeromonas hydrophila* Against New Antibiotics", *Antibacterial Agents & Chemotherapy,* pp 513–514 (Sep. 1982).

Altorfer, et al., "Growth of Aeromonas spp. on Cefsulodin–Irgasan–Novobiocin Agar Selective for *Yersinia entero-co–litica*", Journal of Clinical Microbiology, pp 478–480 (Oct. 1985).

* cited by examiner

*Primary Examiner*—David Guzo
*Assistant Examiner*—David A. Lambertson
(74) *Attorney, Agent, or Firm*—Hendricks & Associates

(57) ABSTRACT

An improved method for detection of total coliforms and *E. coli* comprising a broth containing an ingredient that will encourage growth and repair of injured coliforms, buffers to maintain a pH in the range of 6.5–8, at least one agent that suppresses growth of gram positive cocci and spore-forming organisms, at least one active agent that will suppress growth of non-coliform gram negative bacteria, and at least one chromogen or fluorogen has been used effectively and is cost effective. In the preferred embodiment, both a fluorogen and chromogen were used. Preferred methods include use of filter and/or plates containing the growth-promoting ingredients and the indicators.

10 Claims, No Drawings

METHOD FOR DETECTION OF TOTAL COLIFORMS AND E. COLI

This application is a continuation of U.S. Ser. No. 09/369,173, filed Aug. 5, 1999 now U.S. Pat. No. 6,306,621, which is a continuation-in-part of U.S. Ser. No. 08/117,342 filed Sep. 7, 1993, now U.S. Pat. No. 6,063,590, which is a file-wrapper continuation of U.S. Ser. No. 07/793,881 filed Nov. 18, 1991 now abandoned.

FIELD OF THE INVENTION

This invention is related to means for simultaneous detection of total coliform bacteria and *E. coli*. The medium is particularly useful for routine testing of drinking water. A preferred medium of the invention contains a 4-methylumbel-liferyl-β-D-galactopyranoside (MUGal) and indoxyl-β-D-glucuronide (IBDG) (also known as MI medium) as indicators of the total coliforms (TC) and *E. coli*, respectively.

BACKGROUND OF THE INVENTION

The testing of water in certified laboratories for both total coliforms (TC) and *E. coli* at present is usually accomplished using two different tests. Testing of water for drinking and recreation use requires much time. Other samples that are frequently tested for TC and/or *E. coli* include urine samples (human and veterinary), foods, drugs, and pharmaceuticals. Testing of waste water, aerosols, soil and sludge are sometimes required to evaluate the need for control of harmful organisms.

Drinking water regulations under the Final Coliform Rule require that TC-positive drinking water samples be examined for the presence of *E. coli* or fecal coliforms. Use of current membrane filter technology to detect total and fecal coliforms necessitates concurrent or serial analyses using two different types of media incubated at two different temperatures. Some of the promulgated prior art *E.coli* testing methods are confirmatory tests, not primary isolation procedures. The combined procedures (total coliform test and either fecal coliform test or *E. coli* method) take 28 to 48 hours. The Most Probable Number technology can take up to 72 hours.

Currently, there is no single membrane filter method either in general usage or by approval of the U.S. Environmental Protection Agency that can detect total coliforms and *E. coli* simultaneously in water.

The media available present several deficiencies. Most, as previously mentioned, detect only one organism or group of organisms, and so require the use of two different tests. For example, they may test for either fecal coliforms or total coliforms or for *E. coli*. The use of two media analyzed either concurrently or serially will require many resources in time, labor, materials, equipment, and laboratory space. Some methods now used require one specific enzyme substrate to identify one target organism or group and use methods without enzymatic substrate for another group. Hence, two set-ups and types of media are required to meet the requirements of the regulations.

Many of the methods presently employed do not use isolation media. (They do not result in isolation of organisms directly from the sample.) Such tests are used to confirm the identity of organisms isolated on another medium. The over-all result is delay while two-step processes are accomplished to evaluate the extent of contamination.

Several tests use liquid media in a Most Probable Number (MPN) test format that permits the statistical estimation, but not enumeration, of the target organisms. Although the regulations only require the detection of the presence or absence of organisms, enumeration is useful in determining the extent of contamination and in monitoring remediation. The MPN procedure has a built-in positive bias and tends to overestimate the numbers of organisms present. This bias may result in apparent increased compliance violations and rejection of acceptable drinking water.

Many tests use ingredients that are insufficiently effective in recovering the target organisms. Failure of recovery may also result from use of elevated incubation temperatures required by some testing protocols. Elevated temperatures can result in retardation of growth or prevention of the recovery of injured organisms in the sample.

In many instances, the media are useful only for a limited range of samples. For example, it may be necessary to have a different medium for urine specimens than that for water, and a third medium may be needed to test food.

Two commercially available liquid MPN media are available in tests called Colilert and ColiSure. It is stated that both total coliforms and *E. coli* are detected by these tests simultaneously within 24 to 28 hours. Colilert utilizes 2-nitrophenyl-β-D-galactopyranoside (ONPG) and ColiSure uses chlorophenol red-β-D-galactoside as substrates to test for β-galactoside. Both utilize 4-methyl-umbelliferyl-β-D-glucuronide to test for β-glucuronidase.

These media are expensive. The tests may be used to detect presence or absence of target organisms and/or may result in an estimate of numbers of organisms rather than in an enumeration of target organisms. Both tests have been approved by the USEPA to test for total coliforms and for *E. coli* detection in drinking water. Concern about the high false negative rate of Colilert with disinfected drinking water has been raised by Clark, et. al. (Clark, et. al., Abstract, *Annu. Meet. Am. Soc. Microbiol.* (1990) Q8, p. 289).

The following definitions are used in relation to substrates for detection of organisms:

A chromogen (or chromogenic substrate) is a substance, (usually colorless) that is acted upon by an enzyme to produce a pigment or dye.

A chromophore is a group on or part of a chromogen that produces a color when the chromogen is cleaved by an enzyme.

A fluorogen (or fluorogenic substrate) is a non-fluorescent material that is acted upon by an enzyme to produce a fluorescent compound.

A fluorophore is a group on or part of a fluorogen that is responsible for the fluorescence when a fluorogen is cleaved by an enzyme. (Galactoside is another term for galactopyranoside.)

U.S. Pat. No. 4,923,804 to Ley, et al., teaches use of β-glucuronides to test for *E. coli* and that the indoxyl-β-D-glucuronide is a preferred agent. (See Ex. 2 of the reference cited) However, he teaches, at column 1, l. 50–68 that the use of MUG compounds to test for *E. coli* on a membrane filter test is not appropriate since the fluorescent light can be subject to interference in a membrane filter test. Hence, the teaching of Ley would discourage one from use of an agent having a 4-methylumbelliferyl fluorescent moiety in a membrane filter test. The medium differs from the substrate of the invention in several respects, 1) The medium of Ley can only detect *E. coli* and does not provide for detection of total coliforms. Because of this, a second medium would be required to identify total coliforms, thereby increasing the time, labor, material, and cost to the laboratory performing the analysis. 2) The base medium of Ley contains glycerol as a nutrient and lacks an inducer and an inhibitor of gram negative bacteria that can give a false positive response. Glycerol in media also causes spreading of colonies making enumeration and discrimination difficult. 3) The medium of Ley is incubated at an elevated temperature (44.5° C.) that would be detrimental to the recovery of injured microorganisms.

U.S. Pat. No. 4,591,554 to Koumura, et al., discloses use of fluorescence analysis using umbelliferone derivatives, including phosphates and galactosides. That reference also teaches use of lactose as an inducer. The organisms are first inoculated into broth for growth. There is no inhibitor in the media, and the reference indicates, at column 3, lines 40–45 that the test also picks up Erwinia, Proteus, and Salmonella—gram negative organisms not usually classified among the coliform bacteria. The media recommended by Koumura can also promote the growth of many other types of organisms such as gram positive bacteria, yeasts and fungi that may also be present in the samples. (See Table 2 of that reference.) Some of the non-coliform organisms are able to inhibit the growth of coliforms. Hence, the tests of Koumura are not appropriate for use wherein there is a desire to find the total coliform populations.

Babelona, et al., (*J. Micro. Meth.* 12: 235–245) discloses use of MU-glucuronide complexes in testing for *E. coli* as does much of the prior art. There is no test using a non-fluorescing chromogen-glucuronide to test for *E. coli*, nor is there any MU-galactoside test for total coliforms.

An agar medium developed by Petzel and Hartman (*Appl. Environ. Microbiology.* Vol 24: 925–933) used a selective medium for total coliform identification combined with detection of *E. coli* using 4-methylumbelliferyl-β-D glucuronide. Problems with this medium include the inability to use standard diluents, a high false positive rate when high levels of Flavobacterium species or oxidase positive organisms were present in the water samples, and difficulty distinguishing the natural fluorescence of Pseudomonads from the fluorescence produced during substrate breakdown. Furthermore, this medium could not be used for precise enumeration of the target organisms because of the large number of other Gram negative bacteria that grew on it.

An agar medium using two different enzyme substrates and a different base medium than those used in the MUGal-IBDG Agar (also known as MI agar) of the invention was developed in Germany to simultaneously detect both total coliforms and *E. coli*. Total coliform colonies were identified by the production of blue color from the β-galactosidase cleavage of the substrate X-gal (5-bromo-4-chloro-3-indolyl-β-D-galacto-pyranoside), while *E. coli* colonies were detected by the fluorescence of 4-methylumbelliferone, produced by the cleavage of 4-methylumbelliferyl-β-D-glucuronide by β-glucuronidase (Manafi and Kneifel, *Zbl. Hyg.* 189: 225–234). The reference teaches the use of broth or agar containing 4-methylumbelliferyl-β-D-glucuronide (MUG) and a galactoside with a non-fluorescing chromophore (X-Gal). It also teaches a 4-methylumbelliferyl-β-D-galactoside (MUGal) with a glucuronide attached to a non-fluorescing chromophore, 4-nitrophenyl-β-D-glucuronide (PNPG), in an agar medium containing bile salts to inhibit the growth of organisms that are not coliform bacteria. It is reported that the results of use of this media to test drinking water were not good (p. 230). Manafi attributes his difficulties to the color of the drinking water and the reagent. Manafi indicates that effectiveness of reagents on solid and liquid media differs.

Manafi, et al., *Microbiological Rev.* 55: 335–348 (1991), is a general review article about fluorogenic and chromogenic substrates used in bacterial diagnostics. The particular preferred fluorogenic and chromogenic agents and nutrient substrates used in the invention are not taught therein, and no guidance is provided therein regarding use of inhibitors as required by the instant invention.

DETAILED DESCRIPTION OF THE INVENTION

It is the purpose of this invention to provide a bacterial growth medium that will support repair and growth of total coliform bacteria, including *E. coli,* while suppressing the growth of gram positive cocci and spore-forming organisms and gram negative organisms that would give a false positive reading. The media of the invention may also contain an inducer.

It is a further object of the invention to provide a means of detecting and enumerating both total coliforms (TC) and *E. coli* simultaneously. The method of the invention simplifies compliance with the Final Coliform Rule of EPA and prevents rejection of acceptable drinking water that may occur due to the recovery of thermotolerant species other than *E. coli* with fecal coliform media. Only one incubator is needed (35° C.), and the 35° C. incubation temperature permits the growth of both types of target organisms with the maximum recovery of injured organisms. The method of the invention is both sensitive and specific. False positive and negative rates for *Escherichia coli* are lower than results on other media. *Flavobacterium* species and Aeromonas, typical false positive organisms on other coliform media, are inhibited. This method recovers significantly more total coliforms and *E. coli* than other media tested (mEndo, mTEC). It can be used to show only the presence or absence of Total Coliforms and *Escherichia coli*, if desired.

The preferred embodiment of the invention uses familiar membrane filter technology. The media of the invention are less expensive than Colilert or ColiSure and will be even less expensive when widely used. The media of the invention are useful with several types of water such as drinking water, recreational water, surface water, treatment plant wastewater effluents, water from distribution lines, bottled water, aquaculture and ground water. The media may be used in testing with other types of samples as well. It is possible to use other media disclosed herein for other applications to detect TC and/or *E. coli*.

The medium may also be useful for the isolation and separation of *E. coli* transformants through the use of either or both of their *lac Z* or *uid A* (also referred to as *GUS A* or *gur A*) reporter genes.

EXAMPLE

Medium Formulation

This medium incorporates two different enzyme substrates to simultaneously identify two different types of bacteria (total coliforms and *E. coli*) by means of their specific enzyme reactions in a selective base agar that favors the growth of Gram negative organisms in general and that of coliforms and *E. coli* in particular. The agar medium has the following formulation in grams/liter:

| Ingredient | Amount (g/l) |
| --- | --- |
| Proteose Peptone #3 | 5.0 |
| Yeast Extract | 3.0 |
| β-D-Lactose | 1.0 |
| 4-Methylumbelliferyl-β-D-Galactopyranoside (MUGal) (final concentration 100 μg/ml) | 0.1 |
| Indoxyl-β-D-Glucuronide (IBDG) (final concentration 320 μg/ml) | 0.32 |
| NaCl | 7.5 |
| $K_2HPO_4$ | 3.3 |
| $KH_2PO_4$ | 1.0 |
| Sodium Lauryl Sulfate | 0.2 |
| Sodium Desoxycholate | 0.1 |
| Agar | 15.0 |
| Distilled Water | 1000 milliliters |

The medium was autoclaved for 15 minutes at 121° C., and 5 ml of a freshly-prepared 1 mg/ml filter sterilized solution of Cefsulodin (5 μg/ml final concentration) were added per liter of tempered (50° C.) agar medium. The medium was pipetted into 9×50 mm Petri dishes (5 ml/plate) or other containers as described below.

The substrate MUGal was used to identify total coliforms. These organisms produce the enzyme β-Galactosidase which cleaves the MUGal to produce 4-Methylumbelliferone, a compound that makes the bacterial colonies or growth fluoresce bluish white when exposed to long wave ultraviolet light ($\lambda$=366 nm). Non-coliform colonies do not fluoresce. The substrate IBDG was included to detect the growth of *E. coli*. These organisms produce the enzyme β-Glucuronidase which cleaves the substrate to form a blue color (indigo) in the colonies or growth. Since *E. coli* is also a total coliform and hence, produces β-galactosidase, the blue colonies fluoresce (blue-green) under long wave ultraviolet light. Organisms other than *E. coli* do not generally produce the blue color.

Proteose peptone #3 and yeast extract, common medium ingredients, were added to encourage the growth of the bacteria and the repair of injured organisms. Agar acted as a nutrient and solidifying agent in the medium. Sodium lauryl sulfate and sodium desoxycholate were used to inhibit Gram positive cocci and spore-forming organisms, but not the Gram negative enteric bacteria (e.g., coliforms and *E. coli*) The salts (NaCl, $K_2HPO_4$ and $KH_2PO_4$) were used as nutrients and helped to maintain a neutral pH, thereby preventing the detrimental accumulation of acid from the breakdown of lactose and other nutrients. A small amount of β-D-lactose was added as a general nutrient and to induce β-galactosidase production by the total coliforms.

The antibiotic Cefsulodin was used to inhibit Gram positive bacteria and some non-coliform Gram negative organisms that can cause false positive reactions. The Cefsulodin may be used at rate of 1 to 25 mg/L.

Results

Test Procedure

One-milliliter or larger volumes of samples or their dilutions, prepared in phosphate-buffered dilution water, or dilutions of bacterial cultures, were filtered through 0.45-μm pore size cellulose ester membrane filters, and the filters were aseptically placed on the surface of the agar plates. The plates were incubated at 35° C. for 16–24 hours, and the colonies that grew were inspected for blue color (i.e., production of indigo from IBDG by the *E. coli* enzyme β-glucuronidase), fluorescence under long wave ultraviolet light (i.e., production of 4-Methylumbelliferone from MUGal by the total coliform enzyme β-galactosidase), or both. For optimal differentiation of fluorescent and non-fluorescent colonies, the ultraviolet lamp was held at a distance of about 6"from the plates. Counts were made of the total coliforms and *E. coli* found. In some instances, only the presence or absence of each was noted.

Although most *E. coli* can grow at elevated temperatures (40–45° C.), many other coliforms cannot. Therefore, the medium should be incubated at 35–37° C. for 16–24 hours for maximum growth of both organisms. (Growth can also occur at temperatures as low as 20° C., though much more slowly.) Although only 100 μg/ml MUGal and 320 μg/ml IBDG are recommended because of cost, larger amounts of MuGal (e.g., 200 μg/ml) and IBDG (up to 800 μg/ml) will also work satisfactorily. IBDG can be autoclaved in the medium. Other forms of MUGal and/or IBDG (e.g., the cyclohexylammonium salt of IBDG) or compounds producing the same or a substituted final product (e.g., a 5-Bromo-4-Chloro-3-Indolyl-β-D-Glucuronic acid salt (for example, sodium or cyclohexylammonium salts), commonly referred to as X-GLUC can be used in similar or different amounts.) Different β-Galactosidase substrates (e.g., Chlorophenol Red-β-D-Galactopyranoside or Resorufin-β-D-Galactopyranoside) or β-Glucuronidase substrates can be used successfully in this base medium, but the concentrations must be adjusted for each compound. Filters of other compositions (e.g., cellulose nitrate) and other pore sizes from 0.22–0.8 μm will also work in this method.

To illustrate the specificity and selectivity of MUGal-IBDG Agar for total coliforms and *E. coli*, two sets of analyses were performed. First, dilutions of known bacterial cultures were filtered using the test procedure described above, and the filters were placed on plates of MUGal-IBDG Agar (MI Agar). After incubation at 35° C. for 16–24 hours, the plates were observed for blue color, fluorescence, or both. The results are shown in Table 1.

TABLE 1

REACTIONS OF SEVERAL BACTERIA ON MUGAL-IBDG AGAR

| | Reactions on MUGal-IBDG Agar: | |
| --- | --- | --- |
| Test Organism | Blue Color (β-Gluc[1]) | Fluorescence (β-Gal[2]) |
| *Escherichia coli* (EPA 206) | + | + |
| *Escherichia coli* (ATCC 25922) | + | + |
| *Enterobacter aerogenes* (EPA 202) | − | + |
| *Klebsiella pneumoniae* (EPA 207) | − | + |
| *Citrobacter freundii* (ATCC 8090) | − | + |
| *Pseudomonas aeruginosa* (ATCC 27853) | − | − |

[1]β-Gluc, β-Glucuronidase activity.
[2]β-Gal, β-Galactosidase activity.

In the second test, a series of natural water samples (chlorinated drinking water, groundwater, effluent, and surface water) were filtered, and colonies of each type (blue, fluorescent; non-blue, fluorescent; non-blue, non-fluorescent; blue, non-fluorescent) were counted. Some of each type were picked from MUGal-IBDG Agar for identification using API 20E strips. Similar volumes of each sample were filtered, and the filters were placed on coliform (mEndo Agar) and *E. coli* (mTEC Agar) comparison media. After incubation of the media at their appropriate times and temperatures, target and non-target/background colonies were counted and compared with the corresponding counts on MUGal-IBDG Agar. The formula of the example was designated "MI" medium.

Results of the recovery study showed that the new medium recovered significantly more total coliforms and *E. coli* than the comparison media, and that the number of background colonies on MUGal-IBDG Agar (MI Agar) was significantly less than the corresponding values on the other media. Of the blue colonies picked for identification, 95.7% ($^{66}/_{69}$) were *E. coli,* and 93.1% ($^{161}/_{173}$) of the fluorescent, non-blue colonies were total coliforms. In addition, 93.8% ($^{61}/_{65}$) of the background (non-blue, non-fluorescent) colonies were found to be non-coliforms. The reactions of some representative isolates from the natural water samples are shown in Table 2.

TABLE 2

REACTIONS OF SEVERAL BACTERIAL ISOLATES ON MUGAL-IBDG AGAR

| Organism Identified | Reactions on MUGal-IBDG Agar: | |
|---|---|---|
| | Blue Color ($\beta$-Gluc[1]) | Fluorescence ($\beta$-Gal[2]) |
| *Escherichia coli* | + | + |
| *Klebsiella pneumoniae* | − | + |
| *Klebsiella ozonae* | − | + |
| *Klebsiella oxytoca* | − | + |
| *Citrobacter freundii* | − | + |
| *Citrobacter amalonaticus* | − | + |
| *Enterobacter cloacae* | − | + |
| *Enterobacter aerogenes* | − | + |
| *Enterobacter agglomerans* | − | + |
| *Pseudomonas aeruginosa* | − | − |
| *Salmonella* species | − | − |
| *Aeromonas hydrophila* | − | − |
| *Yersinia enterocolitica* | − | − |
| *Achromobacter* species | − | − |
| *Acinetobacter calco.* var *lwoffi* | − | − |

[1]$\beta$-Gluc, $\beta$-Glucuronidase activity.
[2]$\beta$-Gal, $\beta$-Galactosidase activity.

The results from the two sets of analyses showed that the medium successfully distinguished between *E. coli*, total coliforms, and background or non-coliform organisms using the two enzyme substrates in a unique basal medium.

Various alternative methods of practicing the invention would be understood to be possible by those of skill in the art. Following are examples of possible alternative means. The media of the invention may also be used in confirmation tests wherein bacterial growth samples are taken from primary cultures grown from the test sample.

Alternative 1. MUGal-IBDG Agar (MI Agar) in Spread, Swab, or Streak Plates

The agar medium was prepared as before, poured into 9×50 mm (5 ml/plate) or 50×100 mm (15–20 ml/plate) Petri dishes, and allowed to harden. A small quantity of bacterial culture or sample was applied to and spread on the surface of the agar plates (with or without a membrane filter) by means of an inoculating needle or loop, a cotton swab, a toothpick, a pipette, a glass hockey stick, or other means. The plates were incubated inverted at 35° C. for 8–24 hours, and the growth was observed as before for the presence of blue color and/or fluorescence under long wave ultraviolet light (366 nm). The results of spreading several cultures on this medium are shown in Table 3.

TABLE 3

REACTIONS OF SEVERAL BACTERIA ON MUGAL-IBDG AGAR

| Test Organism | Reactions on MUGal-IBDG Agar: | |
|---|---|---|
| | Blue Color ($\beta$-Gluc[1]) | Fluorescence ($\beta$-Gal[2]) |
| *Escherichi coli* (EPA 206) | + | + |
| *Escherichia coli* (ATCC 25922) | + | + |
| *Enterobacter aerogenes* (EPA 202) | − | + |
| *Klebsiella pneumoniae* (EPA 207) | − | + |
| *Pseudomonas aeruginosa* (ATCC 27853) | − | − |

[1]$\beta$-Gluc, $\beta$-Glucuronidase activity.
[2]$\beta$-Gal, $\beta$-Galactosidase activity.

Alternative 2. MUGal-IBDG Agar (MI Agar) as a Pour Plate

One to two milliliter aliquots of bacterial cultures or samples and/or dilutions of cultures or samples in phosphate-buffered dilution water were pipetted into sterile 15×100 mm Petri dishes. About 15–20 ml of the tempered agar, prepared as before, was added to each plate, and the plate was gently swirled to mix the bacteria with the agar. The plates were allowed to harden and were incubated inverted at 35° C. for 16–24 hours. Colonies were observed for the presence of blue color light and/or fluorescence under long wave ultraviolet light (366 nm). The results obtained with several cultures were the same as those shown in Table 3.

Alternative 3. MUGal-IBDG Agar (MI Agar) in Slants or Stab Cultures

The agar was prepared as before, and 10-ml aliquots were pipetted into sterile screw-cap tubes. The agar was allowed to harden in the upright vertical position for stab cultures or at an angle for slant cultures. The cultures were inoculated by stabbing with an inoculating needle or streaking with a loop, swab, or other means, respectively, and observed for the typical blue color and/or fluorescence as before. The results with several bacterial cultures were the same as those shown in Table 3.

Alternative 4. MUGal-IBDG as a Liquid Medium (Without the Agar) (also called MI medium or broth)

The liquid media exemplified below are made in the same manner as the medium of the example, except that the agar is omitted.

(4a) Use with Absorbent Pads

Aliquots of 1.8–3.0 ml of sterile broth were pipetted onto sterile absorbent pads that had been aseptically placed in 9×50 mm Petri dishes. Cultures or samples, or dilutions of them, were filtered through 0.45-$\mu$m pore size cellulose ester membrane filters as before, and the filters were placed on top of the pads saturated with the broth. (Cultures may also be applied to filters by other means known in the art such as by loop or swab.) The plates were incubated inverted for 8–24 hours, and colonies (or growth) were observed for blue color and/or fluorescence, as previously described. Results with several bacterial cultures were the same as those shown in Table 3.

(4b) Most-Probable Number (MPN) Method

Single-and double-strength liquid media were prepared as in the example except that the agar was omitted and, for double-strength media, all amounts except the water were doubled. The media were pipetted into sterile tubes in 10-ml volumes. Ten-milliliter volumes of a drinking water sample were inoculated into 10 tubes of double-strength medium. The tubes were incubated for 16–24 hours, and observed for blue-green color and/or precipitate (indicating the presence of E. coli) and/or fluorescence under long wave ultraviolet light (366 nm) (indicating the presence of total coliforms). A tube of uninoculated medium (negative control) was also incubated and used as a comparator tube to identify the positive and negative tubes. Other types of samples were analyzed using this method or the standard 5-tube, 3-dilution (or amount) MPN format. In the latter method, each of three different amounts or dilutions of sample were inoculated into five tubes. Volumes of 10-ml were pipetted into double-strength medium tubes, and 1-ml volumes of samples, cultures, or their dilutions were placed in tubes of single-strength medium. The 15-tube test was incubated and observed as before. In either format, the numbers of positive tubes for each type of organism (i.e., E. coli or total coliforms) were counted for each dilution or volume and compared with standard 5-or 10-tube MPN tables to determine the estimated number of organisms per 100 ml sample. (Alternately, 100 ml of double-strength broth could be inoculated with 100 ml of drinking water to determine the presence or absence of the target organisms.)

(4c) Microtiter Confirmation/Identification Test

The liquid medium was prepared as before, and aliquots were pipetted into each well of a sterile microtiter plate (2-ml into each well of the 24-well plate or 200-μl into each well of a 96-well microtiter plate). (Smaller volumes could be placed into plates with more wells.) The plates were inoculated with bacterial strains to be tested and incubated at 35° C. for up to 24 hours. The wells were observed for blue-green color under ambient light and/or fluorescence under long wave ultraviolet light (366 nm). The results with several bacterial strains were similar to those shown in Table 3. This medium could also be used in other types of devices for sample analysis such as IDEXX QUANTITRAY™) Natural samples can also be analyzed for presence or absence of E. coli and/or total coliforms using this method, and the procedure can be automated.

(4d) Confirmatory Tube Test

The liquid medium was prepared as described above, and 10-ml volumes were aseptically pipetted into sterile screw-cap tubes. Bacterial cultures or small amounts of growth from a slant, stab, or isolated colony were inoculated into the media tubes. After incubation at 35° C. for up to 24 hours, the tubes were observed for the blue-green color (or precipitate) under ambient light and/or fluorescence under long wave ultraviolet light. The color reactions with the same five cultures used before were similar to those shown in Table 3.

Alternative 5. Use of the Enzymes Substrates in a Confirmatory Spot Test for Total Coliforms and E. coli One hundred microliter volumes of a bacterial suspension were placed in three wells of a sterile porcelain spot test plate or other suitable plate with wells. The bacterial suspension was obtained in one of the following ways:

1. A loopful of bacterial growth from a slant or an isolated colony from an agar plate was emulsified in a small amount of the liquid MI broth medium without substrates or other non-selective broths.
2. Aliquots of 100 μl of a bacterial culture grown overnight at 35° C. in a non-selective broth or the liquid medium without substrates were used.

Sixty microliters of a freshly-prepared, filter-sterilized 16 mg/ml IBDG solution was added to one well of bacterial suspension, and 300 μl of a freshly-prepared, filter-sterilized 1 mg/ml MUGal solution was added to a second well. The third well, containing only bacterial suspension (negative control), was used as a comparator to distinguish positive and negative wells. Additional wells were inoculated with uninoculated medium, IBDG, and MUGal as controls. The plates were covered with sterile foil and incubated at 35° C. for up to 24 hours. Wells were observed for blue color or fluoresence under long wave ultraviolet light (366 nm) at hourly intervals, as positive reactions have been observed within a few hours. Results of spot tests with several cultures are shown in Table 4. This test could also be performed by adding all of the test liquids and culture or sample to a piece of filter paper or to an absorbent pad and observing the reactions.

TABLE 4

COLOR REACTIONS OF
SEVERAL BACTERIA IN THE SPOT TEST

| Test ORGANISM | Reactions in Wells Containing: | | |
|---|---|---|---|
| | IBDG[1] | MUGal[2] | No IBDG NO MUGal[3] |
| Escherichia coli (EPA 206) | + | + | –/– |
| Escherichia coli (ATCC 25922) | + | + | –/– |
| Enterobacter aerogenes (EPA 202) | – | + | –/– |
| Klebsiella pneumoniae (EPA 207) | – | + | –/– |
| Pseudomonas aeruginosa (ATCC 27853) | – | – | –/– |
| Medium only[4] . (No bacteria) | – | – | –/– |

[1]A positive reaction is shown by production of a blue color in the well.
[2]A positive reaction is shown by fluorescence of the well under long wave ultraviolet light.
[3]Negative controls and comparator wells. The two negatives indicate no blue color and no fluorescence in the wells.
[4]Reagent and medium controls.
Note: The other temperatures, amounts, etc., described in the example of the preferred embodiment also apply to the alternate embodiments.

The selective base medium without the substrates MUGal and IBDG (with or without agar) can be used with other β-galactosidase and β-glucuronidase substrates for the detection of total coliforms and/or E. coli. For example, each of three other β-galactosidase substrates (2-Nitrophenyl-β-D-galactopyranoside, Chlorophenol Red-β-galactopyranoside, and Resorufin-β-D-Galactopyranoside) have been tested with IBDG in this lab. The colors of the total coliform colonies were yellow, orchid, and pink-red, respectively, and the E. coli colonies were varying shades of blue. We believe other combinations of substrates in this base medium would also work in the various embodiments described in this document, and different enzyme substrates (other than β-galactosidase and β-glucuronidase substrates) for specific coliforms could be used in this base medium because of its selectivity. The following guidance is provided for choosing ingredients for the alternative embodiments.

Two chromogenic and/or fluorogenic enzyme substrates are needed in this selective base medium: one is a δ-D-galactoside (or δ-D-galactopyranoside) with an attached chromophore or fluorophore that is specifically cleaved by the enzyme δ-D-galactosidase, produced by total coliform bacteria, and the other is a δ-D-glucuronide (or δ-D-glucuronic acid) with an attached chromophore or fluorophore that is specifically cleaved by the enzyme δ-glucuronidase, produced by *Escherichia coli*. The two substrates should be colorless or non-fluorescent or may not produce the color of fluorescence used to identify the target organism until cleaved by their specific enzyme. Two chromogens, two fluorogens, or a chromogen and a fluorogen may be used if the criteria listed below are met. It is desirable that the chromogens or fluorogens produce one or more compounds after enzyme cleavage that are usable to the target microorganisms.

If two chromogens are used, two different contrasting-color chromophores should be produced upon specific enzyme cleavage, and a third distinct color should be produced by the presence of both colors in the colonies of organisms that have both enzymes. All three colors should be easily distinguished from one another. Both substrates usually remain colorless until cleaved by their specific enzymes and should not spontaneously breakdown in the medium.

If a chromogen and a fluorogen are used, the color or fluorescence, respectively, from one compound should not interfere with the discrimination and/or interpretation of the other. The chromogen should not exhibit non-specific or interfering natural fluorescence under the conditions used for the fluorogen, and the fluorogen should not produce an interfering color under conditions used for the chromogen.

If two fluorogens are used, the two compounds should have considerably different excitation and emission wavelengths or be easily distinguished from one another. In addition, organisms that produce both enzymes should be easily distinguished from those producing only one enzyme.

The substrates, separately or in combination, should not be toxic or inhibitory to either of the target microorganisms and should not encourage the growth of the non-target or background organisms. Inhibition of the non-target bacteria and/or enhancement of the growth of the target microorganisms is desirable.

Upon cleavage, chromogens should produce insoluble or only slightly soluble chromophores that will remain localized in the bacterial colonies. Similarly, fluorophores should not diffuse away from the colonies, as excessive diffusion hinders target colony recognition, discrimination, and enumeration. However, diffusion of color or fluorescence is not a disadvantage in some tests using liquid media, sucn as MPN or other tests performed in tubes.

It is desirable that the chromogens and/or fluorogens be water-soluble and/or be able to withstand autoclaving without breaking down. Alternatively, filter-sterilized solutions can be added after autoclaving. In addition, the substrates should be stable in the medium, should not break down spontaneously, and should not interact with or be detrimentally affected by the other medium ingredients. Chromogens and/or fluorogens can be dissolved in organic solvents and added to the medium if it can be shown that the solvents are neither toxic nor inhibitory to either of the target organisms and do not interact or interfere with the other ingredients or their untilization in any way.

If enzymes other than β-D-galactosidase and β-D-glucuronidase are used to detect other specific coliforms in this selective base medium, the chromogen(s) and/or fluorogen(s) utilized should be specific for the enzyme(s) and should meet the other applicable criteria listed above.

Antibiotics or chemicals other than Cefsulodin may be used as inhibitors of Gram positive and false positive, Gram negative bacteria if they are stable in the medium, do not interact detrimentally with the other medium ingredients, and are not toxic or inhibitory to either of the two target organisms. Antibiotics may be added before autoclaving if their effectiveness is not diminished during autoclaving.

The proteose peptone #3 and yeast extract exemplified may be replaced with other ingredients that encourage growth of bacteria and repair of injured organisms. Failure to provide for repair of injured organisms may result in lower recovery and/or false negative results.

The sodium lauryl sulfate and sodium desoxycholate may be replaced with other chemicals (including other salts) which inhibit Gram positive cocci and spore-forming organisms, but not the Gram negative enteric bacteria. However, the salts exemplified are both inexpensive and readily available and do not injure the target organisms in the stated concentrations, all important factors in choosing inhibiting chemicals for use in these media.

The buffering salts (NaCl, $K_2HPO_4$ and $KH_2PO_4$) can be replaced with other buffers if those buffers perform similarly in this medium and do not adversely affect target organism growth, recovery, and/or discrimination. However, metabolizing organisms may break down or convert some buffers to compounds that may affect the chromogenic and/or fluorogenic substrates, their chromophores or fluorophores.

The use of an inducer (β-D-lactose was exemplified) is optional. However, in media lacking the lactose the colonies were less discrete. Hence, it was felt the addition of such an inducer was advantageous.

| CHROMOGEN AND FLUOROGEN ABBREVIATIONS | |
|---|---|
| X-Gluc | 5-Bromo-4-Chloro-3-Indolyl-Beta-D-glucuronic Acid, sodium salt or cyclohexylammonium salt |
| MUGluc | 4-Methylumbelliferyl-Beta-D-glucuronide |
| Red Gal | 6-Chloro-3-Indolyl-Beta-D-galactoside |
| Red Gluc | 6-Chloro-3-Indolyl-Beta-D-glucuronic Acid, mono-cyclohexylammonium salt |
| X-Gal | 5-Bromo-4-Chloro-3-Indolyl-Beta-D-galactoside |
| IBDG | Indoxyl-Beta-D-glucuronide, sodium salt or cyclohexylammonium salt |
| MUGal | 4-Methylumbelliferyl-Beta-D-galactopyranoside |

Other Combinations of Chromogens and Fluorogens that Work in this Selective Medium:
1. Red Gal and X-Gluc (Either the sodium salt or the cyclohexylammonium salt) Best: 200 mg/l and 50 mg/l respectively Ranges: 200–800 mg/l and 25–320 mg/l, respectively Appearance
  Total coliforms: dusty rose to maroon *E. coli*: cadet blue (grey-blue)
  2. X-Gal and Red Gluc Best: 50 mg/l and 400 mg/l, respectively Ranges: 50–200 mg/l and 200–400 (or more) mg/l, respectively Appearance
  Total coliforms: aquamarine/light turquoise *E. coli*: Dark cadet blue
  3. MUGal and Red Gluc Best: 100 mg/l and 400 mg/l, respectively Ranges: 50–200 mg/l and 200–400 (or more) mg/l, respectively Appearance Total Coliforms: blue-white fluorescense under long wave ultraviolet light (366 nm) *E. coli*: dusty rose (ordinary light), blue-purple fluorescence under long wave ultraviolet light. Note: Ordinarily the double fluorescence would be a problem, but the colors of the fluorescence are different in this instance.

4. Red Gal and IBDG (Either the sodium salt or the cyclohexylammonium salt) Best: 200 mg/l and 320 mg/l, respectively Ranges: 200–800 mg/l and 200–800 mg/l, respectively Appearance Total coliforms: dusty rose to maroon *E. coli*: blue-violet X-Gal and MUGluc Best: 50 mg/l and 100 mg/l, respectively Ranges: 50–200 mg/l and 50–200 mg/l, respectively Appearance Total coliforms: aquamarine/light turquoise *E. coli*: blue-white halo around a dark blue center under long wave ultraviolet light (366 nm)

6. MUGal and X-Gluc Best: 100 mg/l and 50–100 mg/l, respectively Range: 50–200 mg/l and 10–320 mg/l, respectively Appearance:

Total coliforms: blue-white florescence in long wave ultraviolet light (366 nm) *E. coli*: turquoise An advantage of the method of the invention is that it is quite cost effective. For example, the cost of most agar plates is $.03 to $.07. The cost of the plates in using this method ranged from $.11 to $2.37. The last is the price when purchasing at least 2 g of the Sigma cyclohexylammonium salt of the of IBDG. The cost of the medium containing the sodium salt of IBDG was $.27 per plate and that of the cyclohexylammonium salt was $.32 per plate. Although this price is slightly higher than the media currently used, only one analysis employing one medium and one incubator are required instead of the usual double testing. The use of this agar medium with two chromogens, a chromogen and a fluorogen, or two fluorogens to detect both TC and *E. coli* in one medium results in significant reduction in time, space, materials, equipment and personnel needed to perform TC and *E. coli* testing using prior methods. These savings to the laboratory far exceed the small additional cost of the plates. Furthermore, the liquid Most Probable Number (MPN) and Presence/Absence (PA) media containing chromogens and/or fluorogens (price range: $3.95 to $13.00 per test) sold as Colilert and ColiSure are much more expensive than the media of the invention.

What we claim is:

1. A method of detecting the growth of *E. coli* and/or total coliforms in a liquid sample comprising the steps of:

(1) passing a volume of the liquid to be tested through a membrane filter, (2) placing the filter through which the test liquid has been passed on a plate of growth medium containing a solidifying agent, at least one indicator chosen from galactosides and glucuronides, and an agent used to suppress the growth of non-coliform gram negative bacteria, (3) incubating the plate of medium with the filter adherent thereto for a time sufficient to cause perceptible growth of both total coliforms and *E. coli*, and (4) observing the plate to detect the presence of total coliforms and/or *E. coli*.

2. A method of claim 1 wherein the incubation temperature is 20° to 37° C.

3. A method of claim 1 wherein the solidifying agent is agar.

4. A method of claim 1 wherein the test liquid is water.

5. A method of claim 1 wherein the agent used to suppress the growth of non-coliform gram-negative bacteria is Cefsulodin.

6. A method of claim 5 wherein the Cefsulodin is present at a concentration of from 1 to 25 mg/L.

7. A method of detecting *E. coli* and/or total coliforms in a liquid sample comprising the steps of:

(1) passing a volume of the liquid to be tested through a membrane filter, (2) placing the filter through which the test liquid has been passed onto a support to which a growth medium containing at least one indicator chosen from galactosides and glucuronides, and an agent used to suppress the growth of non-coliform gram-negative bacteria has been applied, (3) incubating the sample of medium on the support with the filter adherent thereto for a time sufficient to cause perceptible growth of total coliforms and/or *E. coli*, and (4) observing the filter to detect the presence of total coliforms and/or *E. coli*.

8. A method of claim 7 wherein the support is a pad.

9. The method of claim 7 wherein the agent used to suppress the growth of non-coliform gram-negative bacteria is Cefsulodin.

10. The method of claim 9 wherein the Cefsulodin is present at a concentration of from 1 to 25 mg/L.

* * * * *